United States Patent
Chung et al.

(10) Patent No.: US 10,801,389 B2
(45) Date of Patent: *Oct. 13, 2020

(54) PARTICULATE MATTER SENSOR AND EXHAUST GAS PURIFICATION SYSTEM HAVING THE SAME

(71) Applicant: AMOTECH CO., LTD., Incheon (KR)

(72) Inventors: Yeon-Soo Chung, Incheon (KR); Soo-Min Oh, Seoul (KR); Eun-Ji Kim, Incheon (KR); Sung-Jin Hong, Suwon (KR)

(73) Assignee: AMOTECH CO., LTD., Incheon (KR)

( * ) Notice: Subject to any disclaimer, the term of this patent is extended or adjusted under 35 U.S.C. 154(b) by 206 days.

This patent is subject to a terminal disclaimer.

(21) Appl. No.: 15/735,162

(22) PCT Filed: Jun. 8, 2016

(86) PCT No.: PCT/KR2016/006044
§ 371 (c)(1),
(2) Date: Dec. 8, 2017

(87) PCT Pub. No.: WO2016/200132
PCT Pub. Date: Dec. 15, 2016

(65) Prior Publication Data
US 2018/0355779 A1    Dec. 13, 2018

(30) Foreign Application Priority Data

Jun. 9, 2015 (KR) .................. 10-2015-0081397
Mar. 31, 2016 (KR) .................. 10-2016-0039712

(51) Int. Cl.
*F01N 9/00* (2006.01)
*F01N 3/021* (2006.01)
(Continued)

(52) U.S. Cl.
CPC .............. *F01N 9/002* (2013.01); *F01N 3/021* (2013.01); *F01N 13/008* (2013.01);
(Continued)

(58) Field of Classification Search
CPC ....... F01N 11/00; F01N 2550/04; F01N 3/021; F01N 11/002; F01N 13/10; F01N 3/103;
(Continued)

(56) References Cited

U.S. PATENT DOCUMENTS 6,634,210 B1 * 10/2003 Bosch ................ G01N 15/0656
                                                                    204/426
8,225,640 B2 * 7/2012 Nelson ............... G01N 15/0656
                                                                    73/28.01
(Continued)

FOREIGN PATENT DOCUMENTS

JP    2006515066 A    5/2006
JP    2010190615 A    9/2010
(Continued)

*Primary Examiner* — Randy W Gibson
*Assistant Examiner* — Gedeon M Kidanu
(74) *Attorney, Agent, or Firm* — Bayramoglu Law Offices LLC

(57) ABSTRACT

A particulate matter sensor is provided. The particulate matter sensor includes: an insulating substrate; a first electrode unit, and a plurality of spaced electrodes; a second electrode unit and a heater unit. Wherein each of the spaced electrode includes a sensing unit, wherein the particulate matter is deposited on the sensing unit, and a capacitor unit is configured on the spaced electrode for measuring capacitance. The plurality of spaced electrodes and the rim electrode are electrically connected when particulate matter is deposited, and thereby the capacitance between the first electrode unit and the second electrode unit can be measured.

14 Claims, 8 Drawing Sheets

(51) Int. Cl.
*F01N 13/00* (2010.01)
*G01N 15/06* (2006.01)
*G01N 33/00* (2006.01)
*G01N 27/22* (2006.01)
*G01N 25/32* (2006.01)
*G01N 15/00* (2006.01)

(52) U.S. Cl.
CPC ..... *G01N 15/0606* (2013.01); *G01N 15/0656* (2013.01); *G01N 25/32* (2013.01); *G01N 27/22* (2013.01); *G01N 33/0036* (2013.01); *F01N 2560/05* (2013.01); *F01N 2560/20* (2013.01); *G01N 2015/0046* (2013.01); *Y02T 10/12* (2013.01); *Y02T 10/40* (2013.01)

(58) Field of Classification Search
CPC .. F01N 2560/08; F01N 2560/20; F01N 9/002; F01N 2560/05; F02M 26/04; G01N 2015/0046; G01N 15/0606; G01N 15/0656; G01M 15/102
See application file for complete search history.

(56) References Cited

U.S. PATENT DOCUMENTS

| | | | |
|---|---|---|---|
| 8,915,119 B2 | 12/2014 | Ueno et al. | |
| 2003/0196499 A1* | 10/2003 | Bosch | G01N 15/0656 73/865.5 |
| 2007/0119233 A1* | 5/2007 | Schnell | G01N 15/0656 73/28.01 |
| 2009/0217737 A1* | 9/2009 | Dorfmueller | F01N 11/002 73/28.01 |
| 2010/0147052 A1* | 6/2010 | Nelson | G01N 15/0656 73/28.01 |
| 2010/0206167 A1* | 8/2010 | Okayama | G01N 27/226 96/19 |
| 2011/0314796 A1 | 12/2011 | Nakamura et al. | |
| 2012/0151992 A1* | 6/2012 | Harada | G01N 15/0656 73/23.33 |
| 2013/0283886 A1* | 10/2013 | Teranishi | G01N 15/0606 73/23.31 |

FOREIGN PATENT DOCUMENTS

| | | |
|---|---|---|
| JP | 2011089791 A | 5/2011 |
| JP | 2012037373 A | 2/2012 |
| JP | 2012127907 A | 7/2012 |
| JP | 2013231627 A | 11/2013 |
| KR | 101593670 B1 | 2/2016 |

* cited by examiner

PARTICULATE MATTER SENSOR AND EXHAUST GAS PURIFICATION SYSTEM HAVING THE SAME

CROSS REFERENCE TO RELATED APPLICATIONS

This application is the national phase entry of International Application No. PCT/KR2016/006044, filed on Jun. 8, 2016, which is based upon and claims priority to Korean Patent Applications 10-2015-0081397, filed on June 9, 2015 and 10-2016-0039712, filed on Mar. 31, 2016. The entire contents of which are incorporated herein by reference.

TECHNICAL FIELD

The present disclosure relates to a particulate matter sensor and an exhaust gas purification system having the same, and more particularly, a particulate matter sensor with improved detection sensitivity and a shortened response time, and an exhaust gas purification system having the same.

BACKGROUND

Generally, interest in an after-treatment device for purifying an exhaust gas has been increasing as emission controls are intensified. In particular, regulations on particulate matter (PM) for diesel vehicles are becoming more stringent.

As a result, the most efficient and practical technique for reducing PM is the use of an exhaust gas reducing apparatus using an exhaust gas filtering device.

Meanwhile, in order to diagnose a failure of the exhaust gas reducing apparatus, a PM sensor is mounted at a rear end of a diesel particulate filter (DPF), and the PM sensor is divided into a resistive type PM sensor and a capacitive type PM sensor.

The resistive type PM sensor among the above-described sensors includes a plurality of external electrodes disposed on a surface thereof to be parallel with each other, and when PM is deposited between the external electrodes, a current flows between the external electrodes by the deposited PM and a change in electrical conductivity of the sensor is measured, so that the PM passing through the exhaust gas particulate filter and discharged to a downstream side is easily detected.

In addition, the capacitive type PM sensor includes a plurality of external electrodes disposed on a surface thereof to be parallel with each other and a plurality of internal electrodes disposed in a vertical direction from the plurality of external electrodes, and a capacitance between the external electrode and the internal electrode is measured using an area of PM deposited between the external electrodes and a distance between the external electrode and the internal electrode, so that the PM passing through the exhaust gas particulate filter and discharged to a downstream side is easily detected.

In addition, as for the resistive type PM sensor and the capacitive type PM sensor, a response time of an initial current formed between the external electrodes may be determined by a speed at which particulates are deposed between the external electrodes.

However, in a conventional PM sensor, since an interval between the external electrodes is formed to be larger than a width of the external electrode, there is a problem that a response time of an initial current according to deposition of particulates is too slow.

In addition, since the area of the external electrode is formed to be smaller than the interval between the external electrodes, there is a problem that a detection sensitivity of a capacitance between the external electrode and the internal electrode is low.

Meanwhile, the plurality of external electrode each include a sensing unit on which PM is deposited and a capacitor unit for measuring a capacitance between the external electrode and the internal electrode, and the sensing unit is formed adjacent to the capacitor unit. Accordingly, when the sensing unit, on which PM is deposited, is exposed to a high temperature exhaust gas, the capacitor unit formed adjacent to the sensing unit is also affected by the temperature of heat transferred from exhaust gas.

However, an insulating substrate constituting the PM sensor has an abrupt change in dielectric constant in a high temperature environment by characteristics of a material thereof. For example, when the insulating substrate is formed of alumina, an abrupt change in dielectric constant occurs at about 600° C.

Accordingly, when the sensing unit is exposed to a high temperature environment at 600° C. or above, the capacitor unit adjacent to the sensing unit is also affected by the high temperature, so the abrupt change in dielectric constant causes difficulty in implementing a constant capacitance between the external electrode and the internal electrode.

That is, when the sensing unit and the capacitor unit are formed adjacent to each other, there is difficulty in measuring a constant capacitance in a high temperature environment at a predetermined temperature or above, thereby causing a limitation in use.

Meanwhile, in order to remove PM deposited on the PM sensor in a refresh process for a reuse, heat is applied to the PM sensor through a heater unit. Accordingly, a temperature of the insulating substrate is increased by the heat applied by the heater. In this case, the temperature of the insulating substrate may be increased generally to 650° C. to 2200° C.

Thus, there is difficulty in using the PM sensor until the temperature of the insulating substrate falls to a predetermined temperature or below after the deposited PM is removed using heat of the heater.

SUMMARY

The present disclosure is directed to providing a particulate matter sensor capable of shortening a response time of a capacitance and improving a detection sensitivity, and an exhaust gas purification system having the same.

Further, the present disclosure is directed to providing a particulate matter sensor capable of realizing a constant capacitance even at a high temperature environment in which a dielectric constant of an insulating substrate is abruptly changed, and an exhaust gas purification system having the same.

Furthermore, the present disclosure is directed to providing a particulate matter sensor capable of being directly used without having a waiting time after a refresh process for a reuse is performed, and an exhaust gas purification system having the same.

One aspect of the present disclosure provides a particulate matter sensor including: an insulating substrate; a first electrode unit formed on a surface of the insulating substrate, and including a rim electrode and a plurality of spaced electrodes that are not electrically connected to the rim electrode; a second electrode unit disposed inside the insulating substrate to be spaced an interval from the first electrode unit, and including a plurality of capacitor electrodes electrically connected to each other such that a capacitance between the first electrode unit and the second electrode unit is measured; and a heater unit disposed inside the insulating substrate to provide heat for removing particulate matter deposited on a sensing unit, wherein the spaced electrode includes the sensing unit on which the particulate matter is deposited and a capacitor unit configured to measure the capacitance, and when the particulate matter is deposited, the spaced electrode is electrically connected to the rim electrode to measure the capacitance between the first electrode unit and the second electrode unit.

The first electrode unit may include a rim electrode disposed to surround the plurality of spaced electrodes and a plurality of extended electrodes extending to be parallel with each other in one direction from the rim electrode, wherein the spaced electrode may be provided with the sensing unit disposed between a pair of the extended electrodes adjacent to each other or between the extended electrode and the rim electrode adjacent to each other.

The rim electrode may include a first connection electrode to which end portions of the plurality of extended electrodes are connected and second connection electrodes extending from both end portions of the first connection electrode to be parallel to the extended electrode. The extended electrodes disposed adjacent to each other may be provided at equal intervals.

The sensing unit and the capacitor unit may have predetermined areas, and a second area of the capacitor unit may be larger than a first area of the sensing unit. For example, the second area of the capacitor unit may be at least twice larger than the first area of the sensing unit.

The sensing unit and the capacitor unit may be spaced apart from each other by a lead unit having a predetermined length and interposed therebetween.

A total length of the lead unit connecting the sensing unit to the capacitor unit may be greater than or equal to a total length of the sensing unit.

The capacitor electrode may have an area corresponding to an area of the capacitor unit.

A total area of the sensing units may be smaller than a total area of the capacitor units.

A dielectric layer may be disposed between the first electrode unit and the second electrode unit.

The particulate matter sensor may further include a temperature sensing unit disposed between the second electrode unit and the heater unit, and controls the heater unit.

The insulating substrate may be formed of alumina or zirconia toughened alumina (ZTA).

The particulate matter sensor may be mounted such that the sensing unit is exposed to an exhaust pipe connected to a rear end of an exhaust gas particulate filter of a vehicle.

Another aspect of the present disclosure provides an exhaust gas purification system including: an exhaust manifold; an exhaust gas particulate filter configured to remove particulates included in exhaust gas discharged from the exhaust manifold; and the above described particulate matter sensor installed at an exit side exhaust pipe connected to the exhaust gas particulate filter to detect particulate matter passing through the exhaust gas particulate filter and escaping to a downstream side.

ADVANTAGEOUS EFFECTS

According to the present disclosure, even when a small amount of particulate matter is deposited, a current flowing area of a first electrode unit is increased, so that a capacitance value between the first electrode unit and a second electrode unit can be amplified.

In addition, since an area of a capacitor unit of a spaced electrode, which substantially changes a capacitance of a particulate matter sensor, is formed to be larger than an area of a sensing unit, detection sensitivity of a capacitance being measured between a first electrode unit and a second electrode unit can be increased.

In addition, since a sensing unit of a spaced electrode is disposed between an extended electrode, a space between the sensing unit and the extended electrode that are to be connected by particulate matter is increased, so that a response time taken to change a capacitance between a first electrode unit and a second electrode unit is shortened.

In addition, a sensing unit on which particulate matter is deposited and a capacitor unit for sensing a capacitance are disposed while being spaced a predetermined interval from each other with a lead unit interposed therebetween, so that a capacitor unit side is kept at a low temperature which does not have an abrupt change, even when the sensing unit is exposed to a high temperature environment, thereby implementing a constant capacitance without being affected by the temperature even at a high temperature environment.

In addition, even when a sensing unit is heated by a heater unit to remove particulate matter deposited on the sensing unit, heat is not applied to a capacitance side that is spaced a predetermined distance from the sensing unit, so that a particulate matter sensor can be reused without a waiting time.

DETAILED DESCRIPTION OF THE INVENTION

Figure 1:
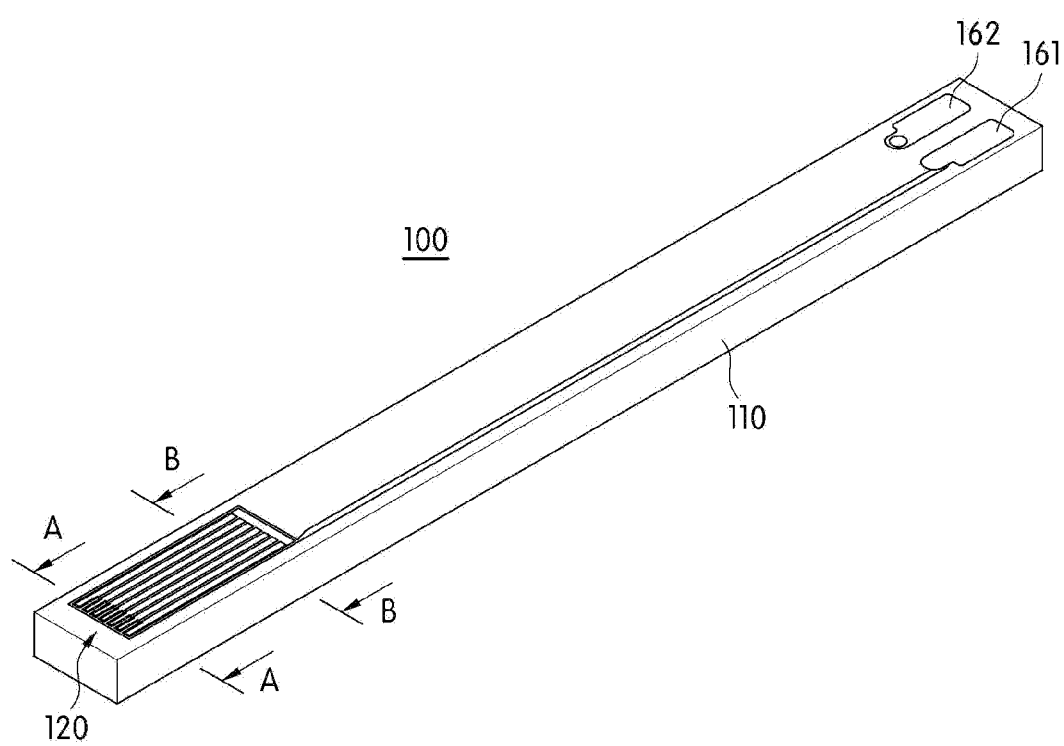
FIG. 1 is a schematic view illustrating a particulate matter sensor according to one embodiment of the present disclosure.

Hereinafter, embodiments of the present disclosure will be described in detail with reference to the accompanying drawings so that those skilled in the art may easily carry out the present disclosure. The present disclosure may be embodied in various ways and is not to be construed as limited to the embodiments set forth herein. In the drawings, parts irrelevant to the description have been omitted for the clarity of description, and the same reference numerals are used to designate the same elements through the whole specification.

Figure 12:
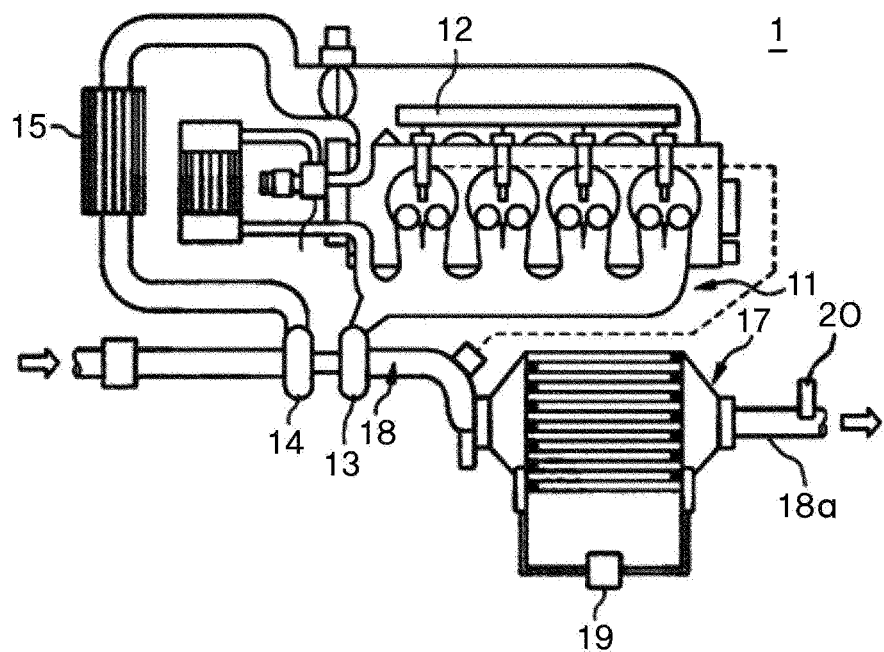
FIG. 12 is a schematic view illustrating an overall configuration of an exhaust gas purification system of a diesel engine for a vehicle to which a particulate matter sensor according to the present disclosure is applicable.

First, referring to FIG. 12, an exhaust gas purification system 1 according to the present disclosure may be configured such that a turbine 13 may be installed on an exhaust manifold 12 of an engine 11, and when a turbo charger 14 rotates in conjunction with the turbine 13, a compressed air may pass through a cooler 15 and be transferred to an intake manifold (not shown), and some combustion exhaust gas discharged from the exhaust manifold 12 may be returned to the intake manifold through a valve 16 and the cooler.

On an exhaust pipe 18 connected to the exhaust manifold 12, diesel oxidation catalyst (not shown) and an exhaust gas particulate filter 17 are installed to process a combustion exhaust gas. That is, the combustion exhaust gas discharged to the exhaust pipe 18 may allow unburned hydrocarbon (HC), carbon monoxide (CO) and nitrogen monoxide (NO) to be oxidized while passing through the diesel oxidation catalyst at an upstream side, and may allow particulate matter, which includes soot, soluble organic fraction (SOF) components, and inorganic components, to be collected while passing through the exhaust gas particulate filter 17 at a downstream side.

The diesel oxidation catalyst may increase an exhaust temperature by oxidation combustion of supplied fuel or oxidize and remove SOF components in the particulate matter, at a time when of forced regeneration of the exhaust gas particulate filter 17 is forcedly regenerated. In addition, $NO_2$ produced by the oxidation of NO may be used as an oxidizing agent for particulate matter deposited on the exhaust gas particulate filter 17 at a rear end of the system, thereby enabling continuous oxidation.

The exhaust gas particulate filter 17 may include a plurality of fine pores passing through a cell wall that partitions gas passages, and may capture particulate matter contained in discharged gas introduced into the exhaust gas particulate filter 17. The exhaust gas particulate filter 17 may be provided in a continuous regeneration type diesel particulate filter having diesel oxidation catalyst integrated with the exhaust gas particulate filter 17.

A differential pressure sensor 19 may be installed on the exhaust pipe 18 to monitor the amount of particulate matter deposited on the exhaust gas particulate filter 17. The differential pressure sensor 19 is connected to an upstream side and a downstream side of the exhaust gas particulate filter 17 to output a signal corresponding to a differential pressure between the upstream side and the downstream side.

In addition, temperature sensors (not shown) are installed on each of the upstream side of the diesel oxidation catalyst and the upstream side and downstream side of the exhaust gas particulate filter 17 to monitor the respective exhaust temperatures.

A control circuit (not shown) monitors a state of catalyst activation in the diesel oxidation catalyst or a state of particulate matter being captured in the exhaust gas particulate filter 17 on the basis of output of the above sensors, and when the amount of particulate matter captured exceeds an allowable amount, performs a forced regeneration to perform a regeneration control to burn and remove particulate matter.

A particulate matter sensor 100, 200 according to the present disclosure may be installed at an exist side exhaust pipe 18a connected to the rear end of the exhaust gas particulate filter 17 to detect particulate matter escaping to the downstream side by passing the exhaust gas particulate filter 17 and the exhaust pipe.

Figure 7:
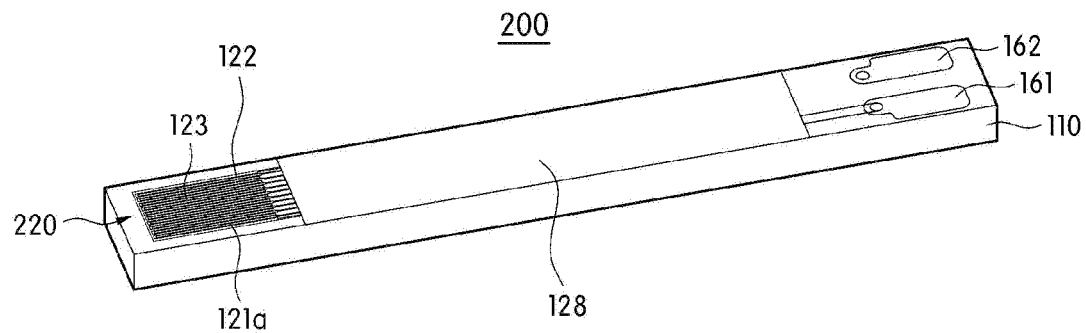
FIG. 7 is a schematic view illustrating a particulate matter sensor according to another embodiment of the present disclosure.

The particulate matter sensors 100 and 200 may each include an insulating substrate 110, a first electrode unit 120 or 220, a second electrode unit 130 or 230, and a heater unit 140 as shown in FIGS. 1 and 7.

The insulating substrate 110 may be formed by stacking a plurality of insulating layers in a height direction, and may be made of an insulator having heat resistance, such as glass, ceramic, spinel, or titanium dioxide.

Figure 2:
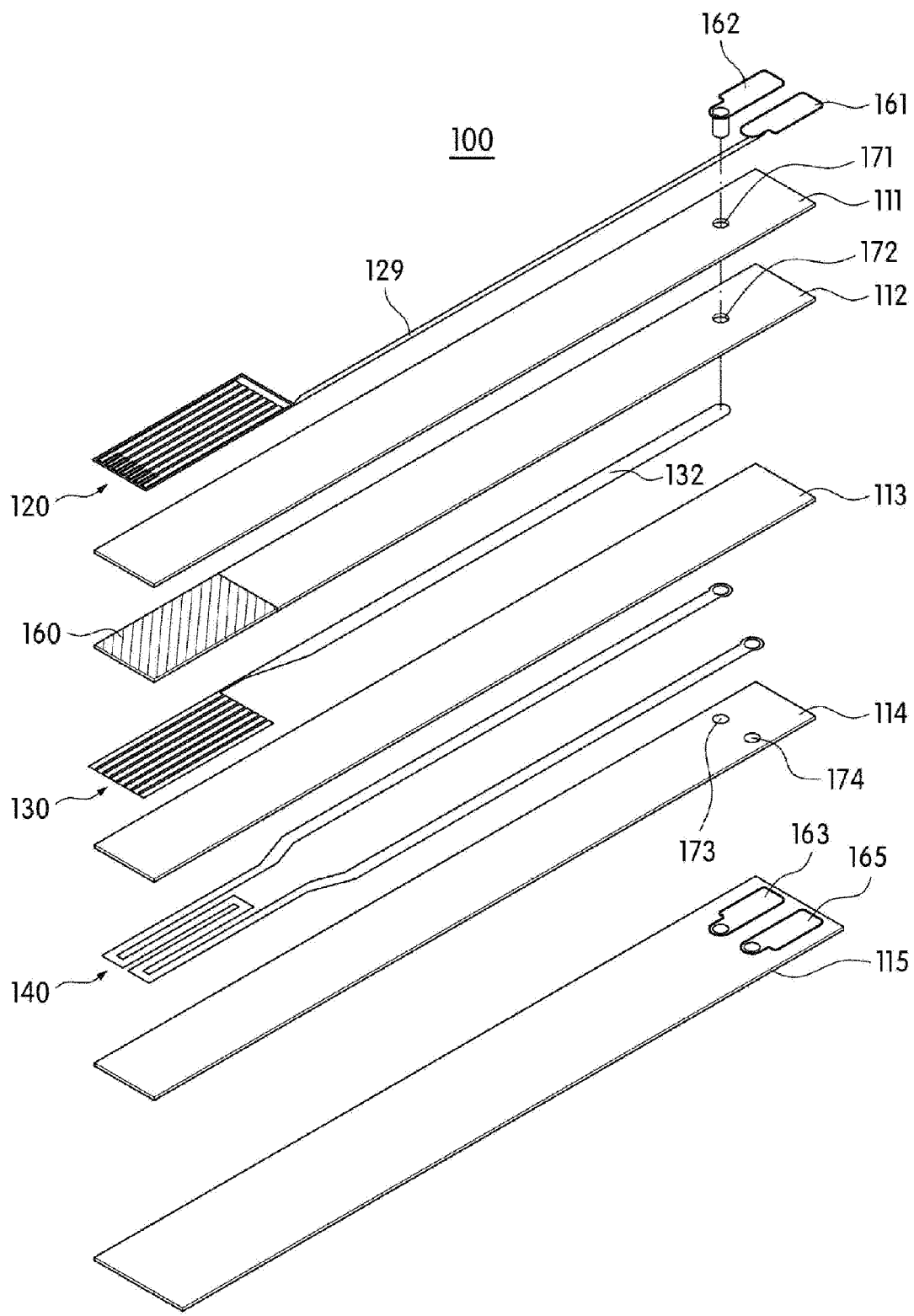
FIG. 2 is an exploded view of FIG. 1.

For example, the insulating substrate 110 may be formed by stacking first to fifth insulating layers 111, 112, 113, 114, and 115 to be parallel with each other as shown in FIG. 2, and the insulating substrate 110 may be formed of alumina or zirconia toughened alumina (ZTA).

However, it should be understood that the type and number of insulating layers forming the insulating substrate 110 are not limited thereto. The number of layers may vary depending on a designing condition.

The first electrode units 120 and 220 may each be provided with at least a portion exposed through a surface of the insulating substrate 110 (see FIGS. 1 and 7).

The first electrode units 120 and 220 may each include a plurality of spaced electrodes 121 or 221, a rim electrode 122, and a plurality of extended electrodes 123.

The plurality of spaced electrodes 121 or 221 may be spaced apart from each other in a width direction of the insulating substrate 110 so as not to be electrically connected to each other as shown in FIGS. 3 to 9.

The plurality of spaced electrodes 121 or 221 may each include a sensing unit 121a and a capacitor unit 121b.

For example, the sensing unit 121a and the capacitor unit 121b having predetermined areas may be formed at both end portions of each of the spaced electrodes 121 and 221.

Here, the sensing unit 121a may be formed in a rectangular shape having a first area, and the capacitor unit 121b may be formed in a rectangular shape having a second area.

In this case, the sensing unit 121a may have a length corresponding to that of the extended electrode 123 while being disposed to be parallel with the extended electrode 123, and may be disposed between the extended electrodes 123 adjacent to each other or may be disposed between the extended electrode 123 and the rim electrode 122 adjacent to each other at an interval from the extended electrode 123 and the rim electrode 122.

Accordingly, a space between the extended electrode 123 and the sensing unit 121a arranged to be parallel with each other and a space between the rim electrode 122 and the sensing unit 121a may form deposition spaces 127 in which particulate matter is deposited.

Accordingly, since particulate matter is deposited in the deposition space 127, the sensing unit 121a and the rim electrode 122 which are not electrically connected may be electrically connected to each other, or the sensing unit 121a and the extended electrode 123 which are not electrically connected may be electrically connected to each other.

The capacitor units 121b are formed at another end portion of the spaced electrodes 121 and 221 and may be electrically connected to each other by particulate matter deposited in the deposition spaces 127. In this way, a current flowing area of the first electrode unit 120 or 220 is sequentially increased, and a change in capacitance between the first electrode unit 120 or 220 and the second electrode unit 130 or 230 may be measured.

In this case, in order to increase the capacitance between the first electrode unit 120 or 220 and the second electrode unit 130 or 230, the second area of the capacitor unit 121*b* may be formed to be larger than the first area of the sensing unit 121*a*.

For example, the second area of the capacitor unit 121*b* may be formed to be at least twice larger than the first area of the sensing unit 121*a*. A width of the capacitor unit 121*b* may be larger than a width of the sensing unit 121*a*.

Accordingly, the capacitance formed between the capacitor unit 121*b* and the second electrode unit 130 or 230 is increased while increasing the detection sensitivity of capacitance.

The rim electrode 122 may be provided in substantially a rectangular frame shape, and disposed to surround the plurality of spaced electrodes 121 and 221, and a side of the rim electrode 122 may be electrically connected to a first electrical connection terminal 161 which is disposed on a surface of the insulating substrate 110, through a lead unit 129.

For example, the rim electrode 122 may include a first connection electrode 122*a*, to which end portions of the extended electrodes 123 are connected, and one pair of second connection electrodes 122*b* extending from both end portions of the first connection electrode 122*a* in a longitudinal direction of the insulating substrate 110, and the one pair of second connection electrodes 122*b* may be connected to each other through a third connection electrode 122*c* having a predetermined length.

Here, the first electrical connection terminal 161 may be disposed to be coplanar with the first electrode unit 120 or 220. In this case, the extended electrode 123 may be provided in a plurality of extended electrodes, and the plurality of extended electrodes 123 may be disposed to be parallel with each other at intervals in a width direction of the insulating substrate 110.

The plurality of extended electrodes 123 may extend inward from the rim electrode 122 to be electrically connected to the rim electrode 122. For example, the plurality of extended electrodes 123 may extend from the first connection electrode 122*a* by a predetermined length in a direction parallel to the second connection electrode 122*b*, and may have an approximately same length as that of the sensing unit 121*a*.

In this case, the plurality of spaced electrodes 121 or 221 may be disposed such that the sensing unit 121*a* is located between the extended electrodes 123 adjacent to each other or between the extended electrode 123 and the second connection electrode 122*b* adjacent to each other, as described above.

Accordingly, in between the extended electrode 123 and the sensing unit 121*a* and between the rim electrode 122 and the sensing unit 121*a*, the deposition spaces 127 in which particulate matter is deposited may be formed.

Figure 3:
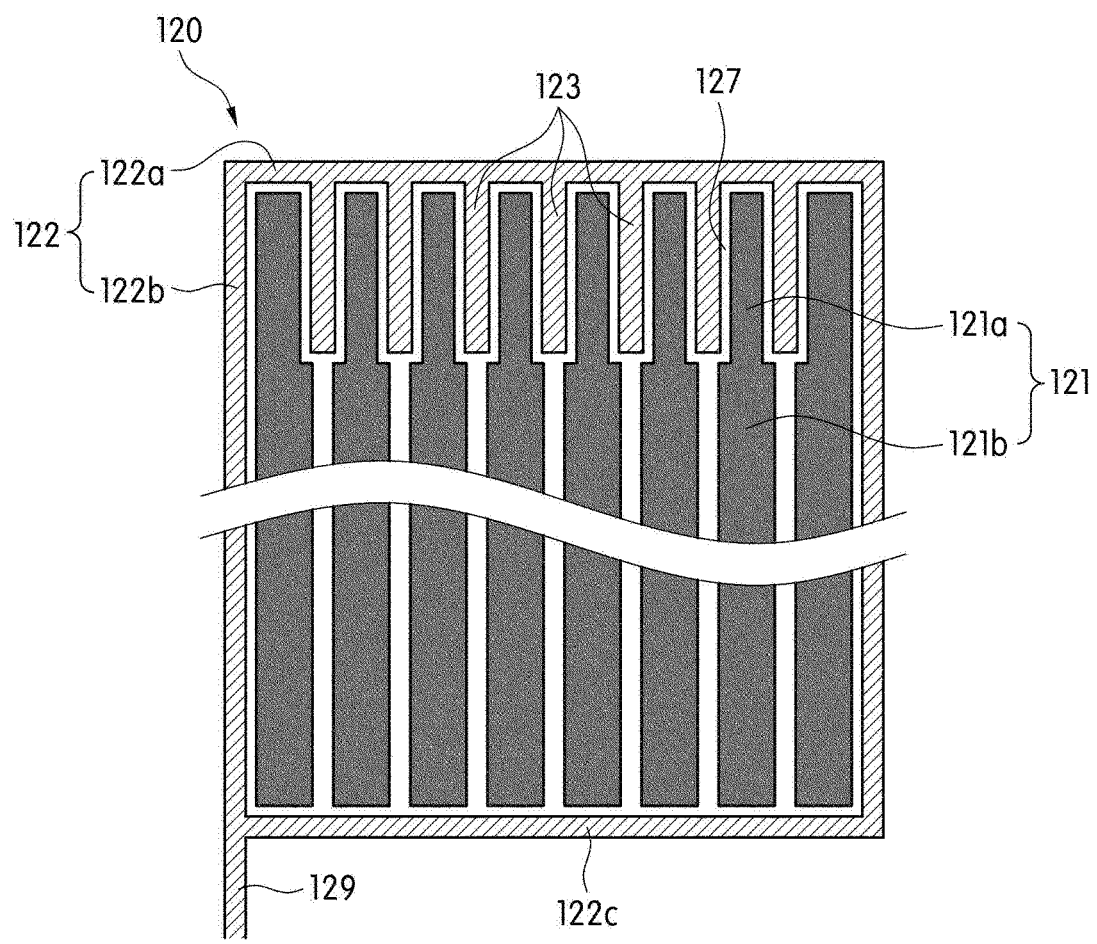
FIG. 3 is an enlarged view of a first electrode unit applied to the particulate matter sensor in FIG. 1.
Figure 10:
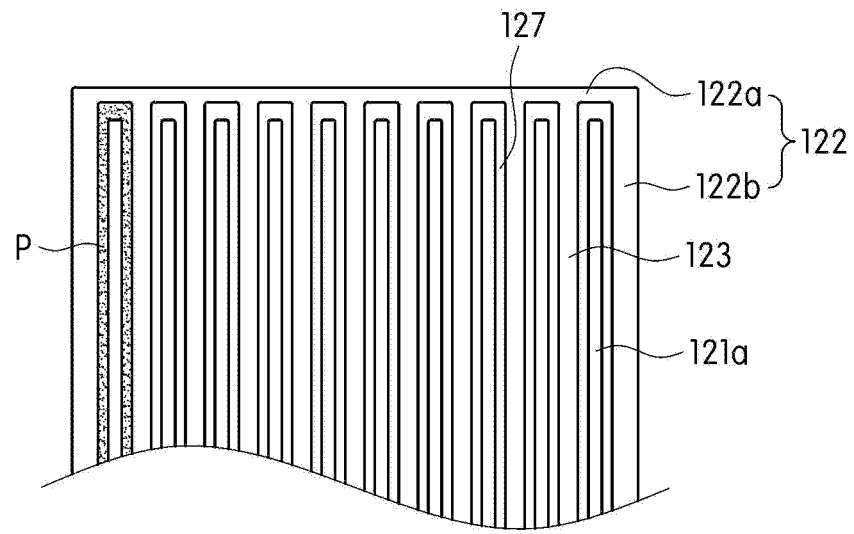
FIG. 10 is a view illustrating a state in which particulate matter is deposited on a sensing unit of a first electrode unit applied to the particulate matter sensor in FIG. 7.

Accordingly, as shown in FIGS. 3 and 10, as particulate matter P is deposited in the deposition spaces 127, the particulate matter causes the second connection electrode 122*b* and the sensing unit 121*a* adjacent to each other to be electrically connected, and cause the extended electrode 123 and the sensing unit 121*a* adjacent to each other to be electrically connected to each other.

In this case, the particulate matter is sequentially deposited in the deposition spaces 127 starting from a first deposition space, so that the plurality of sensing units 121*a* may be sequentially and electrically connected to the rim electrode 122 or the extended electrode 123. Accordingly, the capacitance between the plurality of capacitor units 121*a* and the second electrode unit 130 or 230 may be gradually increased.

Meanwhile, with the particulate matter sensors 100 and 200 according to the present disclosure, the width of the sensing unit 121*a* is provided to be narrower than that of the capacitor unit 121*b*, and the sensing unit 121*a* is disposed between the adjacent extended electrodes 123, so that the number of deposition spaces 127 in which particulate matter is deposited between the sensing unit 121*a* and the extended electrode 123 is increased, and the deposition space 127 in which particulate matter is deposited is provided with a small area. Accordingly, a response time taken to change a capacitance between the capacitor unit 121*b* and a capacitor electrode 131 of the second electrode unit 130 or 230 may be shortened after the spaced electrode 121 or 122 is electrically connected to the rim electrode 122.

The second electrode unit 130 or 230 may be disposed to be parallel with the first electrode unit 120 or 220 inside the insulating substrate 110. In detail, the second electrode unit 130 or 230 may include a plurality of capacitor electrodes 131 corresponding to the capacitor units 121*b*, and the plurality of capacitor electrodes 131 may be disposed at positions corresponding to the positions of the capacitor units 121*b* formed on the plurality of spaced electrodes 121 and 122 (see FIGS. 2 and 8).

Figure 4A:
FIG. 4A is a plan view of a first electrode unit applied to the particulate matter sensor in FIG. 1.
Figure 4B:
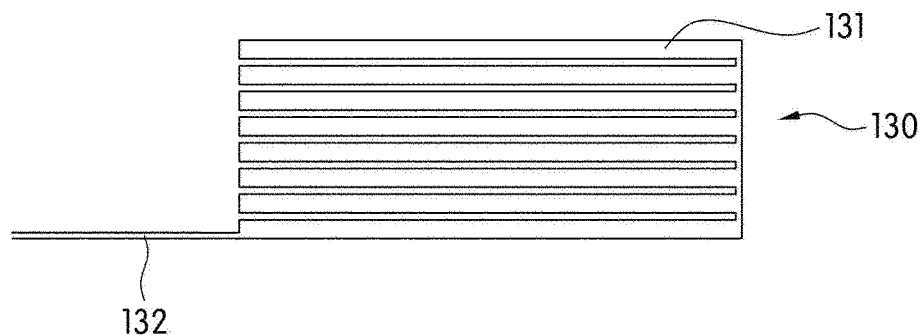
FIG. 4B is a plan view of a second electrode unit applied to the particulate matter sensor in FIG. 1.
Figure 11:
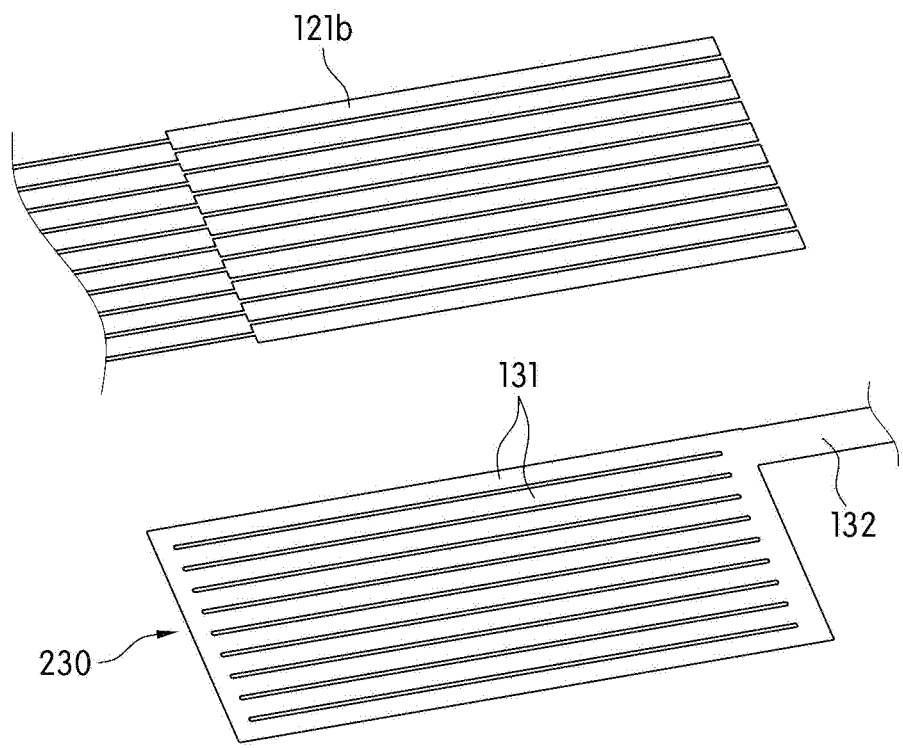
FIG. 11 is a view illustrating a capacitor unit and a second electrode unit applied to the particulate matter sensor in FIG. 7.

Here, the plurality of capacitor electrodes 131 may be electrically connected to each other (see FIGS. 4B and 11). One side of the second electrode unit 130 or 230 may be extended in a longitudinal direction of the insulating substrate 110 by a lead unit 132 and a portion of the second electrode unit 130 or 230 may be electrically connected to a second electrical connection terminal 162 disposed on a surface of the insulating substrate 110 through via hole 171 and 172 or 271 (see FIGS. 2 and 8). In addition, the plurality of capacitor electrodes 131 may be electrically connected to each other at one end portions thereof (see FIG. 4B) or at both end portions thereof (see FIG. 11).

In this case, the second electrical connection terminal 162 may be disposed to be coplanar with the first electrical connection terminal 161, and may be arranged to be parallel with the first electrical connection terminal 161 in a width direction of the insulating substrate 110.

Figure 8:
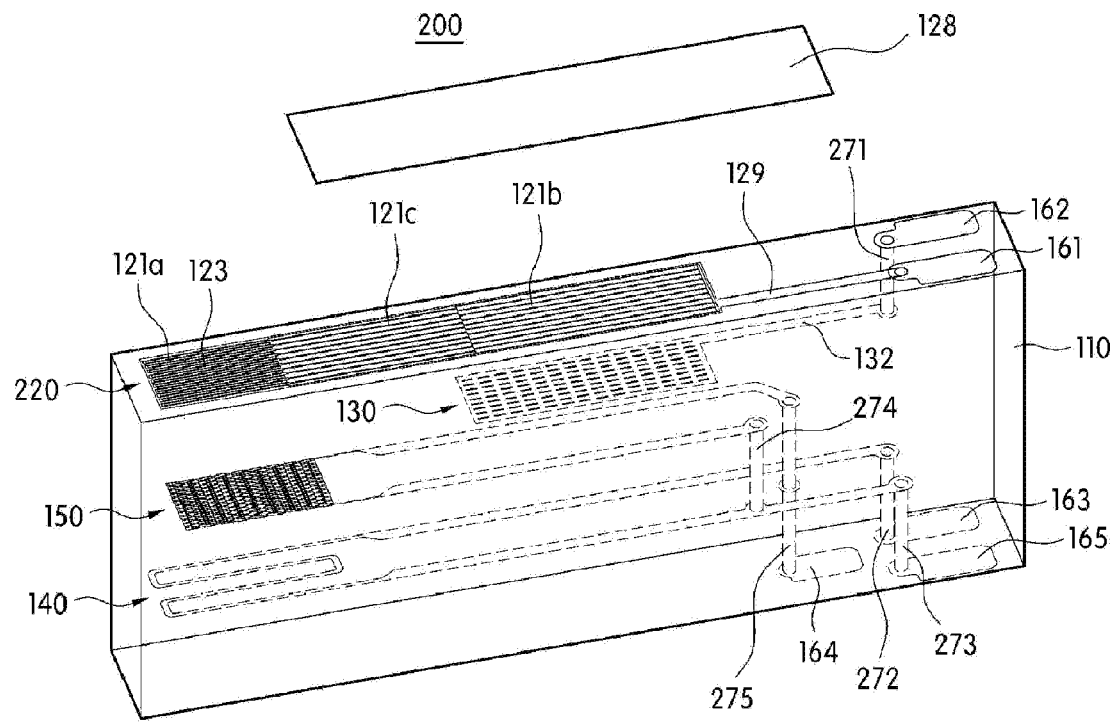
FIG. 8 is a schematic view illustrating a placement relationship of principal components in FIG. 7.

In more detail, the second electrode unit 130 or 230 may be disposed inside the insulating substrate 110 as shown in FIGS. 2 and 8, and the plurality of capacitor electrodes 131 may have predetermined areas corresponding to those of the capacitor units 121*b* of the spaced electrode 121 or 221.

In addition, the plurality of capacitor electrodes 131 may be disposed directly below the capacitor units 121*b* to correspond to the capacitor units 121*b* formed on the spaced electrode 121 or 221.

in addition, the plurality of capacitor units 121*b* and the plurality of capacitor electrodes 131 may be arranged in rows in the longitudinal direction of the insulating substrate 110, and the plurality of capacitor units 121*b* may be arranged to correspond to the plurality of capacitor electrodes 131 in the width direction of the insulating substrate 110.

In this case, the capacitor electrodes 131 may each have approximately the same area as that of the capacitor unit 121*b* corresponding thereto (see FIG. 11), and have the same length as the sum of lengths of the capacitor unit 121*b* and the sensing unit 121*a* (see FIGS. 4A and 4B).

Accordingly, the plurality of capacitor electrodes 131 may each have an area larger than or equal to an area of the capacitor unit 121b corresponding thereto.

Meanwhile, a dielectric layer 160 having a dielectric constant may be disposed between the first electrode unit 120 or 220 and the second electrode unit 130 or 230 vertically arranged in a height direction of the insulating substrate 110 (see FIG. 2). The dielectric layer 160 may be disposed between the capacitor unit 121b of the first electrode unit 120 or 220 and the capacitor electrode 131 of the second electrode unit 130 or 230 to smoothly implement a capacitance characteristic between the capacitor unit 121b of the spaced electrode 121 or 221 and the capacitor electrode 131 of the second electrode unit 130 or 230, and may be formed of a ceramic material.

It should be noted that the first electrode units 120 and 220 and the second electrode units 130 and 230 applied to the particulate matter sensors 100 and 200 according to the present disclosure are not limited to the above-described structure, and may be changed into various shapes.

The heater unit 140 is configured to heat the sensing unit 121a and may be disposed below the first electrode unit 120 or 220 inside the insulating substrate 110. In this case, both end portions of the heater unit 140 may be electrically connected to a third electrical connection terminal 163 and a ground terminal 165 that are provided on a lower surface of the insulating substrate 110 through via holes 173 and 174 or 272 and 273.

Accordingly, when the heater unit 140 heats the sensing unit 121a, particulate matters deposited in the deposition space 127 may be removed.

Here, the heater unit 140 may be formed of a material that is not easily oxidized at a high temperature. This is because an exhaust gas has a high temperature of about 300° C. or above, and at a time of heating by the heater unit 140, a high temperature of about 600° C. or above is formed, so that there is a high possibility of oxidization by the high temperature heat when the heater unit is formed of a general metal.

Figure 9:
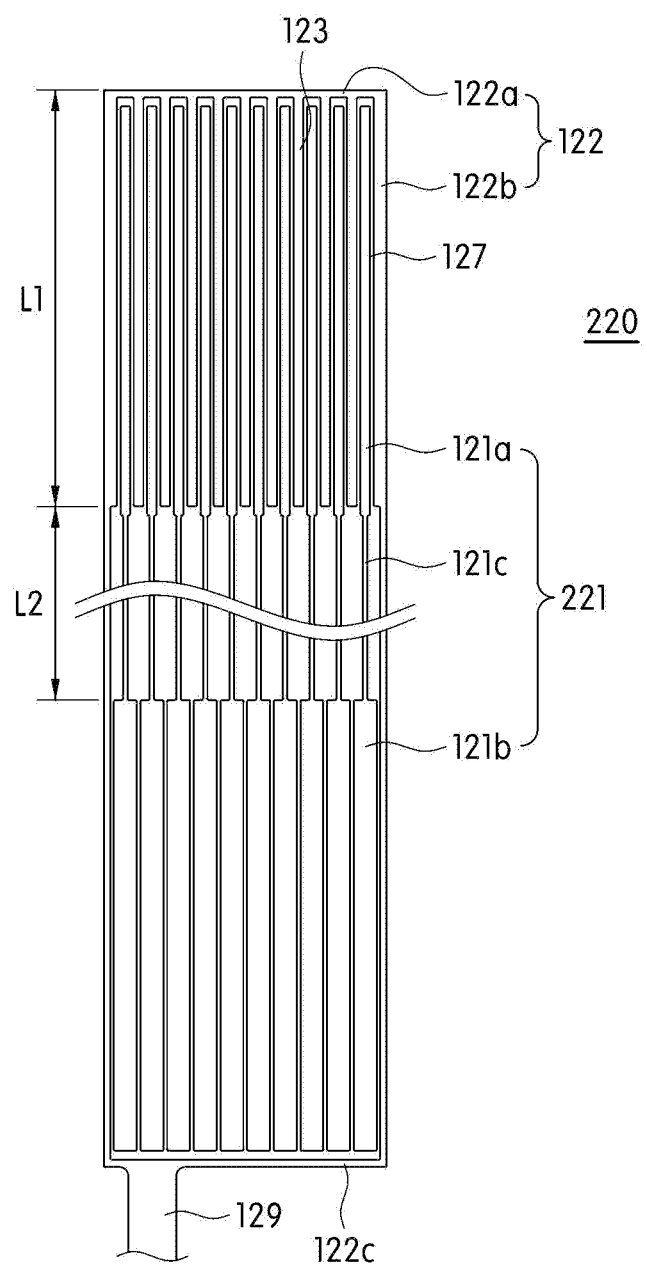
FIG. 9 is a plan view illustrating a first electrode unit applied to the particulate matter sensor in FIG. 7.

Meanwhile, the particulate matter sensor 200 according to one embodiment of the present disclosure may have the sensing unit 121a and the capacitor unit 121b disposed to be spaced a predetermined interval from each other (see FIG. 9).

To this end, the spaced electrode 221 may be provided such that the sensing unit 121a and the capacitor unit 121b, which are formed at opposite sides of the spaced electrode 221, are connected to each other by a lead unit 121c having a predetermined length.

In this case, the capacitor unit 121b may be spaced apart from the sensing unit 121a by an interval that is larger than or equal to a total length of the sensing unit 121a. To this end, a total length L2 of the lead unit 121c may be approximately the same as or larger than a total length L1 of the sensing unit 121a.

In this way, the capacitor unit 121b for measuring a change in capacitance is spaced a predetermined interval from the sensing unit 121a which is exposed to a high temperature environment, so that the capacitor unit 121b may implement a constant capacitance without being affected by the temperature.

In more detail, the sensing unit 121a serves to expand an area in which the first electrode unit 220 is conducted through particulate matter deposited in the deposition space 127, and thus the sensing unit 121a is not significantly affected by a high temperature environment. However, the capacitor unit 121b for measuring a change in capacitance between the first electrode unit 220 and the second electrode unit 230 may implement a constant capacitance at a predetermined temperature or below according to a material forming the insulating substrate 110, but, at the predetermined temperature or above, the dielectric constant is subject to an abrupt change, so there is a difficulty in precisely measuring a change in capacitance.

For example, when the insulating substrate 110 is formed of ceramic, an abrupt change in dielectric constant occurs at about 600° C. by the characteristics of the material. Accordingly, when the capacitor unit 121b is formed adjacent to the sensing unit 121a, the capacitor unit 121b is affected by a temperature and is incapable of implementing a constant capacitance. Accordingly, there is a difficulty in precisely measuring a capacitance at a high temperature environment having a predetermined temperature or above, thereby leading to limitation in use.

However, the particulate matter sensor 200 according to one embodiment of the present disclosure has the capacitor unit 121b and the sensing unit 121a disposed to be spaced apart from each other with the lead unit 121c connecting to each other, so that an abrupt change in dielectric constant at a high temperature is prevented, thereby implementing a constant capacitance even in a high temperature environment.

In addition, even when a temperature of the sensing unit 121a is increased by the heater unit 140, the capacitor unit 121b is kept at a temperature lower than that of the sensing unit 121a, so that a waiting time for reuse is not needed in a refresh process.

Here, the capacitor unit 121b and the lead unit 121c may be covered by an additional insulating layer 128 to be insulated without being exposed to the outside.

Meanwhile, the particulate matter sensor 200 according to one embodiment of the present disclosure may further include a temperature sensing unit 150 configured to measure a temperature inside the insulating substrate 110 or the temperature of the sensing unit 121a (see FIG. 7).

To this end, the temperature sensing unit 150 may be disposed between the sensing unit 121a and the heater unit 140 inside the insulating substrate 110.

Both ends of the temperature sensing unit 150 may be electrically connected to the heater unit 140 and a fourth electrical connection terminal 164 through via holes 274 and 275.

In detail, referring to FIG. 7, one end of the temperature sensing unit 150 may be electrically connected to the heater unit 140 through the via hole 275 connected to the heater unit 140, and the other end of the temperature sensing unit 150 may be electrically connected to the fourth electrical connection terminal 164 formed on the lower surface of the insulating substrate 110 through the via hole 274.

The fourth electrical connection terminal 164 formed on the lower surface of the insulating substrate 110 are not electrically connected to the third electrical connection terminal 163 and the ground terminal 165.

Accordingly, the control circuit (not shown) of the vehicle may control the heater unit 140 to heat the sensing unit 121a by comparing the temperature measured by the temperature sensing unit 150 with the temperature measured by the temperature sensor installed in the vehicle.

Meanwhile, in order to provide an installation area of the temperature sensing unit 150 inside an installation area of the heater unit 140, the temperature sensing unit 150 may be provided with an area smaller than or equal to that of the heater unit 140.

The particulate matter sensor 100 or 200 having the above described constitution may be installed on the exist side exhaust pipe 18a connected to the rear end of the exhaust gas particulate filter 17 of the vehicle, and the sensing unit 121a may be mounted such that the sensing unit 121a is exposed to an exhaust gas.

Accordingly, particulate matter P1 flowing to the exist side exhaust pipe 18a through the exhaust gas particulate filter 17 (see FIG. 12) passes adjacent to the particulate matter sensor 100 or 200 mounted at one side of the exist side exhaust pipe 18a.

Figure 5:
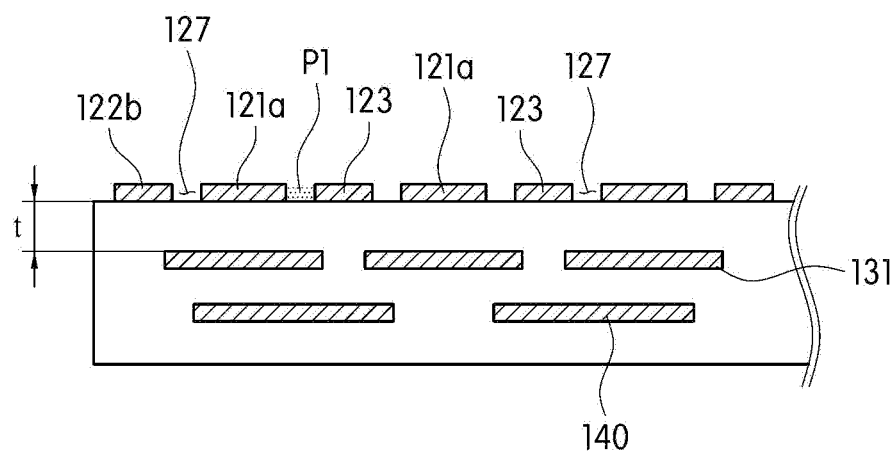
FIG. 5 is a partial cross-sectional view taken along line A-A of FIG. 1.
Figure 6:
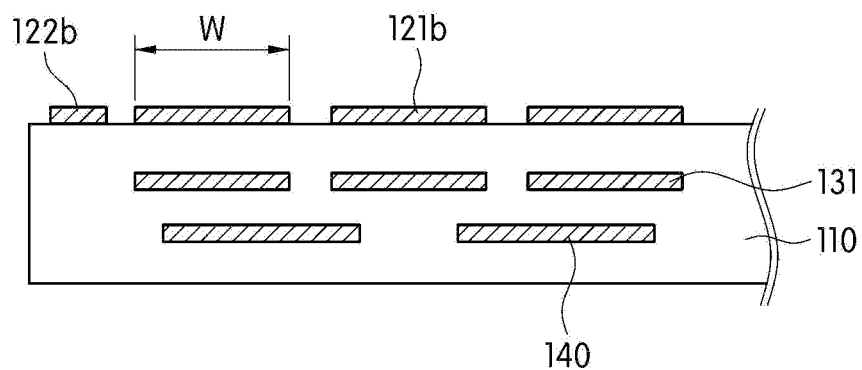
FIG. 6 is a partial cross-sectional view taken along line B-B of FIG. 1.

In this case, the particulate matter P1 may be deposited in the spaces 127 formed between the sensing unit 121a of the spaced electrode 121 or 221 and the extended electrodes 123 as shown in FIGS. 5 and 10.

Accordingly, the sensing unit 121a may be electrically connected to the extended electrode 123 by the particulate matter deposited in the space 127. Accordingly, the current flowing area of the sensing unit 121a that allows a flow of an electrical current is increased, and the capacitor unit 121b integrally formed with the sensing unit 121a is subject to electrical connection, so that a capacitance between the spaced electrode 121 or 221 and the second electrode unit 130 or 230 is changed.

In this case, the capacitance between the capacitor unit 121b and the second electrode unit 130 or 230 may be calculated by Equation 1 below.

$$C = \varepsilon W/t \quad [Equation\ 1]$$

In Equation 1, W denotes an area of the capacitor unit 121b of the spaced electrode electrically connected to the rim electrode, and t denotes a distance between the capacitor unit 121b and the second electrode unit 130 or 230, so that a capacitance between the first electrode unit 120 or 220 and the second electrode unit 130 or 230 may be measured. Here, the second area of the capacitor unit 121b of the spaced electrode 121 or 221 may be larger than the second area of the sensing unit 121a.

As for the particulate matter sensors 100 and 200 according to one embodiment of the present disclosure, an area allowing the measurement of a capacitance when a single sensing unit 121a is electrically connected to the rim electrode 122 corresponds to both of the area of the sensing unit 121a and the area of the capacitor unit 121b. Accordingly, by only having the sensing unit 121a of the spaced electrode 121 or 221 electrically connected to the rim electrode 122, the capacitance between the spaced electrode 121 or 221 and the second electrode unit 130 or 230 may be increased.

In addition, as for the particulate matter sensors 100 and 200 according to one embodiment of the present disclosure, the area of the capacitor unit 121b which changes the capacitance between the capacitor unit 121b and the capacitor electrode 131 is larger than the area of the sensing unit 121a, so that a response time taken to change the capacitance between the spaced electrodes 121 or 221 and the capacitor electrodes 131 may be shortened, and a large change in capacitance may be implemented.

In addition, as for the particulate matter sensors 100 and 200 according to one embodiment of the present disclosure, the area of the sensing unit 121a is smaller than that of the capacitor unit 121b, and the sensing unit 121a is disposed between the extended electrodes 123 of the rim electrode 122, so that the number of contact points connected by the particulate matter between the sensing unit 121a and the rim electrode 122 may be increased, and thus the response time taken to change the capacitance between the spaced electrodes 121 or 221 and the capacitor electrodes 131 may be shortened.

Although exemplary embodiments of the present disclosure have been described, the exemplary embodiments described in the specification are intended to not limit the technical spirit of the present disclosure, and those skilled in the art should appreciate that another embodiment may be easily suggested by additions, modifications, deletions, supplements, and the like made within the scope of the same spirit, and the other embodiment also may be included within the scope and sprit of the present disclosure.

What is claimed is:

1. A particulate matter sensor, comprising:
an insulating substrate;
a first electrode unit, wherein the first electrode is formed on a surface of the insulating substrate, wherein the first electrode unit includes a rim electrode and a plurality of spaced electrodes set apart from each other that are not electrically connected to the rim electrode;
a second electrode unit, wherein the second electrode is disposed inside the insulating substrate to be spaced an interval from the first electrode unit, wherein the second electrode includes a plurality of capacitor electrodes electrically connected to each other such that a capacitance between the first electrode unit and the second electrode unit is measured; and
a heater unit, wherein the heater unit is disposed inside the insulating substrate to provide heat for removing particulate matter deposited on a sensing unit,
wherein each of the spaced electrodes includes a sensing unit spaced from the rim electrode to define a deposition space on which particulate matter is deposited when the particulate matter sensor is secured in a vehicle exhaust stream, and a capacitor unit configured on the spaced electrode to measure the capacitance, and when the particulate matter is deposited on the deposition space, the spaced electrode is electrically connected to the rim electrode to measure the capacitance between the first electrode unit and the second electrode unit,
wherein, the sensing unit and the capacitor unit have predetermined areas formed at both end portions of each of the spaced electrode, wherein a total area of the sensing unit is formed to be smaller than the total area of the capacitor unit so that the particulate matter is sequentially deposited on the deposition space.

2. The particulate matter sensor of claim 1, wherein the plurality of extended electrodes disposed adjacent to each other are provided at equal intervals.

3. The particulate matter sensor of claim 1, wherein the capacitor electrode has an area corresponding to an area of the capacitor unit.

4. The particulate matter sensor of claim 1, wherein a dielectric layer is disposed between the first electrode unit and the second electrode unit.

5. The particulate matter sensor of claim 1, further comprising a temperature sensing unit, wherein the temperature sensing unit is disposed between the second electrode unit and the heater unit to control the heater unit.

6. The particulate matter sensor of claim 1, wherein the insulating substrate is formed of alumina or zirconia toughened alumina (ZTA).

7. The particulate matter sensor of claim 1, wherein the rim electrode is disposed to surround the plurality of spaced electrodes and a plurality of extended electrodes extend to be parallel with each other in one direction from the rim electrode, wherein each of the spaced electrode is provided with the sensing unit disposed between a pair of the extended electrodes adjacent to each other or between the extended electrode and the rim electrode adjacent to each other.

8. The particulate matter sensor of claim 7, wherein the rim electrode includes a first connection electrode and a second connection electrode, wherein a plurality of end portions of the plurality of extended electrodes are connected to the first connection electrode, and the second connection electrode extends from both end portions of the first connection electrode to be parallel to the extended electrode.

9. The particulate matter sensor of claim 1, wherein the sensing unit has a first area, and the capacitor unit has a second area; wherein the second area of the capacitor unit is larger than the first area of the sensing unit.

10. The particulate matter sensor of claim 9, wherein the second area of the capacitor unit is at least twice larger than the first area of the sensing unit.

11. The particulate matter sensor of claim 1, wherein the sensing unit and the capacitor unit are spaced apart from each other by a lead unit having a predetermined length and interposed there between.

12. The particulate matter sensor of claim 11, wherein the lead unit connects the sensing unit to the capacitor unit, wherein a total length of the lead unit is greater than or equal to a total length of the sensing unit.

13. The particulate matter sensor of claim 11, wherein the particulate matter sensor is mounted such that the sensing unit is exposed to an exhaust pipe connected to a rear end of an exhaust gas particulate filter of a vehicle.

14. An exhaust gas purification system, comprising:
an exhaust manifold;
an exhaust gas particulate filter, wherein the exhaust gas particulate filter is configured to remove a plurality of particulates included in exhaust gas discharged from the exhaust manifold; and
a particulate matter sensor, wherein the particulate matter sensor is installed at an exit side exhaust pipe connected to the exhaust gas particulate filter to detect particulate matter passing through the exhaust gas particulate filter and escaping to a downstream side;
wherein the particulate matter sensor comprises:
an insulating substrate;
a first electrode unit, wherein the first electrode is formed on a surface of the insulating substrate, wherein the first electrode unit includes a rim electrode and a plurality of spaced electrodes set apart from each other that are not electrically connected to the rim electrode;
a second electrode unit, wherein the second electrode is disposed inside the insulating substrate to be spaced an interval from the first electrode unit, wherein the second electrode includes a plurality of capacitor electrodes electrically connected to each other such that a capacitance between the first electrode unit and the second electrode unit is measured; and
a heater unit, wherein the heater unit is disposed inside the insulating substrate to provide heat for removing particulate matter deposited on a sensing unit,
wherein each of the spaced electrodes includes a sensing unit spaced from the rim electrode to define a deposition space on which particulate matter is deposited when the particulate matter sensor is secured in a vehicle exhaust stream, and a capacitor unit configured on the spaced electrode to measure the capacitance, and when the particulate matter is deposited on the deposition space, the spaced electrode is electrically connected to the rim electrode to measure the capacitance between the first electrode unit and the second electrode unit,
wherein, the sensing unit and the capacitor unit have predetermined areas formed at both end portions of each of the spaced electrode, wherein a total area of the sensing unit is formed to be smaller than the total area of the capacitor unit so that the particulate matter is sequentially deposited on the deposition space.

* * * * *